United States Patent [19]

Patel et al.

[11] Patent Number: 4,772,473

[45] Date of Patent: Sep. 20, 1988

[54] NITROFURANTOIN DOSAGE FORM

[75] Inventors: Vikram S. Patel; Harry L. Welles, both of Norwich, N.Y.

[73] Assignee: Norwich Eaton Pharmaceuticals, Inc., Norwich, N.Y.

[21] Appl. No.: 874,943

[22] Filed: Jun. 16, 1986

[51] Int. Cl.[4] .................. A61K 9/52; A61K 9/54; A61K 31/345

[52] U.S. Cl. .................. 424/457; 424/80; 424/81; 424/451; 424/452; 424/458; 424/489

[58] Field of Search .................. 424/141, 621, 37, 80, 424/451, 452, 457, 458, 489, 81

[56] References Cited

U.S. PATENT DOCUMENTS

| | | | |
|---|---|---|---|
| 2,610,181 | 9/1952 | Hayes | 548/311 |
| 3,401,221 | 9/1968 | Borgmann et al. | 514/390 |
| 3,427,378 | 2/1969 | Henderson et al. | 424/14 |
| 3,444,290 | 5/1969 | Wai | 424/4 |
| 3,458,622 | 7/1969 | Hill | 424/19 |
| 3,634,584 | 1/1972 | Poole | 424/22 |
| 4,016,254 | 4/1977 | Seager | 424/80 |
| 4,122,157 | 10/1978 | Huber | 424/21 |
| 4,126,672 | 11/1978 | Sheth et al. | 424/22 |
| 4,152,444 | 5/1979 | Vischer et al. | 514/183 |
| 4,252,786 | 2/1981 | Weiss et al. | 424/19 |
| 4,343,789 | 8/1982 | Kawata et al. | 424/78 |
| 4,370,313 | 1/1983 | Davies | 424/32 |
| 4,404,183 | 9/1983 | Kawata et al. | 424/19 |
| 4,610,875 | 9/1986 | Panoz et al. | 424/80 |

FOREIGN PATENT DOCUMENTS 1204580  9/1970  United Kingdom .................. 424/37

OTHER PUBLICATIONS

El Egakey, M. A., "In Vitro and in Vivo Release Studies of Nitrofurantoin from Coated Crystals", *Acta Pharmaceutica Technologica*, vol. 28, No. 4 (1982).

*Primary Examiner*—Shep K. Rose
*Attorney, Agent, or Firm*—Milton B. Graff, IV; David L. Suter; Jack D. Schaeffer

[57] ABSTRACT

The invention involves a combination sustained release/rapid release pharmaceutical capsule for oral administration of nitrofurantoin comprising, in a capsule shell, a first layer of a first particulate mixture comprising nitrofurantoin, polyvinylpyrrolidone and carboxyvinylpolymer; and a second layer of a second particulate mixture comprising macrocrystalline nitrofurantoin.

10 Claims, No Drawings

NITROFURANTOIN DOSAGE FORM

TECHNICAL FIELD

This invention is concerned with a novel dosage unit form of nitrofurantoin. More particularly, it is concerned with a combination sustained release/rapid release capsule dosage unit form of nitrofurantoin comprising carboxyvinylpolymer and polyvinylpyrrolidone.

BACKGROUND OF THE INVENTION

Nitrofurantoin is a well-known antibacterial compound and has been used extensively as an active ingredient in antibacterial pharmaceutical compositions. See, for example, Mintzer, S., E. R. Kadison, W. H. Shlaes & O. Felsenfeld, "Treatment of Urinary Tract Infections with a New Antibacterial Nitrofuran", *Antibiotics & Chemotherapy*, Vol. 3, No. 2 (February 1953), pp. 151–157; Richards, W. A., E. Riss, E. H. Kass & M. Finland, "Nitrofurantoin—Clinical and Laboratory Studies in Urinary Tract Infections", *Archives of Internal Medicine*, Vol. 96 (1955), pp. 437–450; Eudy, W. W., "Correlations Between in Vitro Sensitivity Testing and Therapeutic Response in Urinary Tract Infections", *Urology*, Vol. II, No. 5 (Nov. 1973), pp. 519–587; Bush, I. M., W. I. Metzger, I. Garlovsky, R. B. Bush, R. J. Ablin & N. Sadoughi, "Urinary Tract Infection—Antibacterial Susceptibility Patterns", *Urology*, Vol. III, No. 6 (Jun. 1974), pp. 697–700; Dickey, L., "A Comparison of the In Vitro Effectiveness of Nitrofurantoin and Five Antibiotics Against Bacteria from Urinary Tract Infections", *American Journal of Medical Technology*, (Sept.-Oct. 1961), pp. 273–279; Karmall, M. A., S. DeGrandis & P. C. Fleming, "Antimicrobial Susceptibility of *Campylobacter jejuni* with Special Reference to Resistance Patterns of Canadian Isolates", *Antimicrobial Agents and Chemotherapy*, Vol. 19, No. 4 (1981), pp. 593–597.

Nitrofurantoin is widely used in the treatment of infections of the urinary tract. A side effect which occasionally occurs with the oral administration of nitrofurantoin is that of nausea and emesis. A means for mitigating this side effect of nitrofurantoin is to use macrocrystalline nitrofurantoin as disclosed in U.S. Pat. No. 3,401,221 issued to Borgmann, Hayes, Paul & Paul on Sept. 10, 1968. Macrocrystalline nitrofurantoin has proved to be an excellent drug for treating urinary tract infections with minimal side effects of nausea and emesis. However, macrocrystalline nitrofurantoin must generally be administered orally about four times daily to be effective.

Sustained release pharmaceutical dosage unit forms are well-known, and carboxyvinylpolymer and polyvinylpyrrolidone are substituents known to be used in a variety of sustained release pharmaceutical dosage unit forms.

U.S. Pat. No. 3,458,622 issued to Hill on July 29, 1969, discloses controlled release tablets which are produced by blending a medicament with polyvinylpyrrolidone and carboxyvinylpolymer, granulating, drying, and compressing into tablets. The ratio of polyvinylpyrrolidone:carboxyvinylpolymer in these controlled release tablets is from about 1:10 to 10:1. Hill discloses that "(w)hen the resulting tablet is placed in water or gastric fluid, the two polymeric substances react to form a complex of low solubility which is gumlike in consistency and . . . retards the diffusion of the active material from the tablet." Hill also notes that there is a rapid release of some of the medicament because ". . . the active material near the surface is allowed to diffuse out of the tablet fairly rapidly. As the moisture penetration becomes deeper, the restraining matrix becomes thicker and reduces the diffusion rate of the active substance. When the tablet is transferred to intestinal fluid, . . . the entire matrix is then eroded," thus providing the sustained release of the active substance trapped therein. (See column 1, lines 38–52.)

U.S. Pat. No. 3,634,584 issued to Poole on Jan. 11, 1972, discloses a controlled release tablet in which the controlled release is achieved by combining carboxyvinylpolymer and polyethyleneglycol. Poole achieves a combination of rapid release and sustained release by producing a two-layer tablet, one layer containing the controlled release formulation and the other layer containing a formulation of the active material which disintegrates rapidly to make the active material contained therein quickly available.

El Egakey, M. A., "In vitro and in vivo Release Studies of Nitrofurantoin from Coated Crystals", *Acta Pharmaceutica Technologica*, Vol. 28, No. 4 (1982), pp. 267–271, discloses pharmaceutical dosage forms in which crystals of nitrofurantoin were coated with a mixture of polyvinylpyrrolidone and carboxyvinylpolymer. Sustained release of this dosage form is achieved by having different coated crystal particles release their entrapped nitrofurantoin at different times. The coated crystal particles can be made into a capsule dosage form by filling them into a hard gelatin capsule shell, or can be made into a tablet by compressing them together in a standard tableting operation.

U.S. Pat. Nos. 4,122,157 issued to Huber on Oct. 24, 1978, and 4,370,313 issued to Davies on Jan. 25, 1983, disclose sustained release and delayed release dosage unit forms of nitrofurantoin, respectively.

U.S. Pat. Nos. 4,343,789 and 4,404,183 issued to Kawata, Aruga, Ohmura, Sonobe, Yoneya & Sone on Aug. 10, 1982 and Sept. 12, 1983, respectively, disclose sustained release dosage forms made by dissolving an active material with a polymeric material and then drying the solution to form an amorphous mixture of the active material and polymer. The amorphous material is broken into small particles which are then filled into hard gelatin capsule shells. Either carboxyvinylpolymer or polyvinylpyrrolidone are disclosed as polymeric materials which can be used to produce these sustained release capsules.

U.S. Pat. No. 4,126,672 issued to Sheth & Tossounian on Nov. 21, 1978, discloses sustained release pharmaceutical capsules which are powder mixtures of medicaments with a hydrocolloid or mixture of hydrocolloids. Carboxyvinylpolymer is disclosed as one of the hydrocolloids useful in achieving such sustained release capsules. Sheth & Tossounian discloses that "(u)pon oral ingestion of the sustained release capsules . . . , the capsule shell dissolves leaving the formulation in contact with gastric fluid. Upon contact with gastric fluid, the outermost hydrophyllic colloid hydrates to form an outside barrier which substantially retains the shape of the capsule and therefore acts to prevent the mass from disintegrating." (See column 2, lines 38–44.) These hydrated powder masses swell in gastric fluid such that "they have a bulk density . . . less than one and therefore are buoyant in gastric fluid and thus are retained in a buoyant state in the stomach until substantially all the medicament is released therefrom." (See column 2, lines 10-14.) "(A)fter substantially all the medicaments therein are released, the gelatinous mass disperses." (See column 2, lines 35-37.)

SUMMARY OF THE INVENTION

It is an object of the present invention to provide a dosage unit form of nitrofurantoin which will be an effective treatment for urinary tract infections when orally administered to a patient about twice daily.

It is a further object of the present invention to provide such a dosage unit form of nitrofurantoin which when orally administered to a patient results in minimal side effects of nausea and emesis.

It is also an object of the present invention to provide novel combination sustained release/rapid release pharmaceutical capsules for oral administration of nitrofurantoin.

It is also an object of the present invention to provide a process for producing such combination sustained release/rapid release pharmaceutical capsules.

The present invention involves a combination sustained release/rapid release pharmaceutical capsule for oral administration of nitrofurantoin comprising, in a capsule shell which is soluble in a gastrointestinal juice:
(1) a first layer of a first particulate mixture comprising:
 (a) from about 10% to about 90% of nitrofurantoin;
 (b) from about 5% to about 86% of polyvinylpyrrolidone; and
 (c) from about 4% to about 40% of carboxyvinylpolymer; wherein said polyvinylpyrrolidone and said carboxyvinylpolymer occur substantially entirely in separate particles of said first particulate mixture; and
(2) a second layer of a second particulate mixture comprising macrocrystalline nitrofurantoin.

DETAILED DESCRIPTION OF THE INVENTION

The present invention relates to combination substained release/rapid release pharmaceutical capsules for oral administration of nitrofurantoin in which separate layers of a first particulate mixture and a second particulate mixture are contained in a capsule shell which is soluble in a gastrointestinal juice. "Particulate mixture" as used herein means a mixture of flowable, particulate solids, such as powders, granules, crystals, flakes, etc. "Flowable" as used herein means that under light stress particles of the mixture will move relative to adjacent particles. (The particles of such mixtures may have a moderate tendency to adhere to adjacent particles. For example, some commercial capsule filling machines lightly compress the particulate mixture being filled into capsule shells such that a "plug" of the particulate mixture is formed. Such a plug of material may have sufficient cohesiveness to remain intact with gentle handling outside the capsule shell. However, such a plug of material can be easily broken apart under light pressure, and such material is considered to be flowable herein.) The first particulate mixture comprises nitrofurantoin, polyvinylpyrrolidone, and carboxyvinylpolymer. The second particulate mixture comprises macrocrystalline nitrofurantoin. Preferred pharmaceutical capsules of the present invention also contain other pharmaceutical carriers which aid in the preparation of the capsules. The necessary and optional ingredients are described in detail below.

When a combination sustained release/rapid release pharmaceutical capsule of the present invention is administered orally to a patient, the patient swallows the capsule so that it reaches the stomach intact. The capsule shell is generally of such material such that it dissolves in the acidic gastric juice in the stomach. Upon dissolution of the capsule shell, the gastric juice wets the layers of particulate mixtures that were within the capsule shell. For the layer of the second particulate mixture (comprising macrocrystalline nitrofurantoin), the particles rapidly disperse in the stomach. In this way, a rapid release of nitrofurantoin is made available for absorption into the systemic system. Alternatively, the layer of the second particulate mixture and the layer of the first particulate mixture can be separated from one another by enclosing either layer inside a smaller capsule shell within the capsule shell containing the entire dosage unit form.

For the layer of the first particulate mixture (comprising nitrofurantoin, polyvinylpyrrolidone and carboxyvinylpolymer), instead of the particles dispersing in the gastric juice, the wetting of the outer thickness of the first particulate mixture results in the formation of a cohesive mass which does not disperse or substantially swell but remains intact in the acid stomach medium. Only a small amount of nitrofurantoin diffuses from the cohesive mass as long as it remains in the stomach. Upon passing from the acidic stomach medium to the more alkaline environs of the intestines, the cohesive mass formed from the layer of the first particulate mixture softens and slowly erodes. In this way, a sustained release of nitrofurantoin is made available in the intestines for absorption into the systemic system.

The combination of rapid release and sustained release of nitrofurantoin is preferably regulated by the formulation of the capsules to achieve a therapeutic level of nitrofurantoin in a patient for a period of about twelve hours or more. Capsules which can be used to achieve such duration of a therapeutic level of nitrofurantoin in a patient with minimal side effects of nausea and emesis are described in detail hereinbelow.

Nitrofurantoin

As used herein, "nitrofurantoin" is the compound N-(5-nitro-2-furfurylidene)-1-aminohydantoin, which has the following chemical structure:

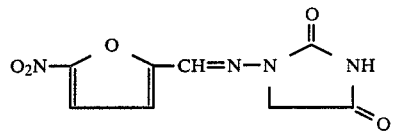

or its pharmaceutically acceptable salts, hydrates, or complexes. (See "6445. Nitrofurantoin", *The Merck Index*, 10th ed. (1983, pp. 946-947.) As used herein, nitrofurantoin "complexes" refer to chemical complexes of nitrofurantoin with other chemical constituents which result in entities which retain at least a substantial portion of the antimicrobial activity of nitrofurantoin. Examples of such complexes include nitrofurantoin-phthaloyl glycine and nitrofurantoin-phthaloyl aminocaproic acid.

A method for preparing nitrofurantoin is disclosed in U.S. Pat. No. 2,610,181 issued to Hayes on Sept. 9, 1952, which is incorporated herein by reference. A method for preparing macrocrystalline nitrofurantoin is disclosed in U.S. Pat. No. 3,401,221 issued to Borgmann, Hayes, Paul & Paul on Sept. 10, 1968, which is incorporated herein by reference. As used herein, "macrocrystalline nitrofurantoin" is particulate crystalline nitrofurantoin where at least 90 weight percent of the crystals have a surface area of from about 120 cm$^2$/gm to about 1,000 cm$^2$/gm. Preferred macrocrystalline nitrofurantoin has at least 90 weight percent of the crystals with a surface area of from about 195 cm$^2$/gm to about 485 cm$^2$/gm. Highly preferred macrocrystalline nitrofurantoin is available commercially from Norwich Eaton Pharmaceuticals, Inc. (Norwich, N.Y.) under the trade name Macrodantin ®.

For nitrofurantoin there is a minimum therapeutic concentration of the active drug that must be reached in certain tissues or the urine of the patient, if the desired treatment is to occur. Sustained release pharmaceutical dosage unit forms of nitrofurantoin such as those disclosed in Huber and El Egakey hereinabove, generally make the nitrofurantoin available a little bit at a time over an extended period of time. Since the nitrofurantoin is metabolized in the body or is eliminated in the urine with time, it may be a very long time or never that it reaches the minimum therapeutic concentration in the desired tissues or the urine, if the sustained release of nitrofurantoin is slow. In order to overcome this, it has been found necessary to provide an initial rapid release dose of nitrofurantoin to rapidly achieve the minimum therapeutic concentration. (Huber provides such rapid release dose of nitrofurantoin with a tablet having two discrete portions, one a slow release portion and one a rapid release portion containing micronized nitrofurantoin.) Once the minimum therapeutic concentration of nitrofurantoin is surpassed in the desired tissue or urine, a sustained release of nitrofurantoin can maintain it by delivering the nitrofurantoin in sufficient quantities to compensate for the amount metabolized by or eliminated from the patient's body.

In developing combination sustained release/rapid release nitrofurantoin dosage unit forms, only a small frequency of nausea and emesis was expected from the use of microcrystalline nitrofurantoin in the rapid release portion, based on previous experiences with small dosages of microcrystalline nitrofurantoin. Instead, it was found that the small amounts of nitrofurantoin provided in the rapid release portion of certain combination dosage unit forms resulted in surprisingly frequent instances of nausea and emesis in patients, when such nitrofurantoin was microcrystalline (smaller crystals than macrocrystalline nitrofurantoin, e.g. micronized or powdered nitrofurantoin).

Although it is known that macrocrystalline nitrofurantoin substantially reduces the side effects of nausea and emesis, a suitable method for incorporating macrocrystalline nitrofurantoin in a combination sustained release/rapid release dosage form was not known or readily apparent. Macrocrystalline nitrofurantoin could not be readily incorporated as a part of a combination sustained release/rapid release tablet, such as that of Huber, since the granulating and tableting operations used to produce the tablets would reduce the size of the macrocrystals such that they would not provide the desired reduction in nausea and emesis. The combined sustained release/rapid release pharmaceutical capsules of the present invention incorporate macrocrystalline nitrofurantoin in the rapid release portion of the dosage unit form, thus mitigating the side effects of nausea and emesis which occur when microcrystalline nitrofurantoin is used in the rapid release portion.

For the combination sustained release/rapid release nitrofurantoin capsules of the present invention, the rapid release (second particulate) mixture comprises from about 10 mg to about 200 mg of macrocrystalline nitrofurantoin per capsule, preferably from about 25 mg to about 100 mg of macrocrystalline nitrofurantoin per capsule, more preferably from about 40 mg to about 60 mg of macrocrystalline nitrofurantoin per capsule.

For the combination sustained release/rapid release pharmaceutical capsules of the present invention, the sustained release (first particulate) mixture comprises from about 10% to about 90% of nitrofurantoin, preferably from about 20% to about 70% of nitrofurantoin, more preferably from about 30% to about 60% of nitrofurantoin. The quantity of nitrofurantoin in the first particulate mixture is from about 50 mg to about 1000 mg per capsule, preferably from about 100 mg to about 400 mg per capsule, more preferably from about 150 mg to about 250 mg per capsule.

For the sustained release (first particulate) mixture, it is important that the nitrofurantoin, the polyvinylpyrrolidone and the carboxyvinylpolymer be substantially uniformly mixed. In order to achieve such a substantially uniform first particulate mixture, it is preferred that the nitrofurantoin have a particle size range similar to that of the polyvinylpyrrolidone and carboxyvinylpolymer. The particle size of the nitrofurantoin in the first particulate mixture preferably is such that 100 percent of particles which will pass through a 60 mesh sieve (U.S. Standard Screen).

Polyvinylpyrrolidone

In the sustained release pharmaceutical capsules of the present invention, it has been found that polyvinylpyrrolidone is a necessary ingredient to achieve sustained release of the nitrofurantoin. As used herein, "polyvinylpyrrolidone" or "PVP" is poly[1-(2-oxo-1-pyrrolidinyl)ethylene]:

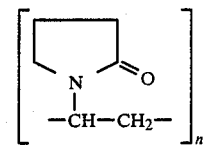

(See "7594. Povidone", *The Merck Index*, tenth ed. (1983), p. 1106.)

Polyvinylpyrrolidone is produced commercially as a series of products having mean molecular weights ranging from about 5,000 to about 1,000,000. Polyvinylpyrrolidone preferably used in the present invention has a mean molecular weight of from about 7,000 to about 700,000.

The primary purpose of the polyvinylpyrrolidone in the sustained release pharmaceutical capsules of the present invention is to provide for the formation of the cohesive mass rapidly upon being wetted by gastrointestinal juice, when the capsule shell is permeated by the juice. Without the presence of polyvinylpyrrolidone in the particulate mixture, either a cohesive mass does not form, or any mass that does form does not have sufficient structure to provide the desired sustained release function. If sufficient polyvinylpyrrolidone is present in the particulate mixture to initially form a stable cohesive mass, a greater percentage of polyvinylpyrrolidone in the particulate mixture has little or no effect on the duration of sustained release of the nitrofurantoin from the cohesive mass.

The particulate mixture of the sustained release pharmaceutical capsules of the present invention comprises from about 5% to about 86% of polyvinylpyrrolidone, preferably from about 10% to about 80% of polyvinylpyrrolidone, more preferably from about 15% to about 70% of polyvinylpyrrolidone, more preferably still from about 20% to about 60% of polyvinylpyrrolidone. The particle size of the polyvinylpyrrolidone in the particulate mixture preferably is such that 100 percent of particles will pass through a 60 mesh sieve (U.S. Standard Screen).

Carboxyvinylpolymer

Carboxyvinylpolymer is another necessary ingredient in order to achieve the sustained release pharmaceutical capsules of the present invention. The term "carboxyvinylpolymer" as used herein describes a family of compounds disclosed and claimed in U.S. Pat. No. 2,798,053 issued to Brown on July. 2, 1957.

A carboxyvinylpolymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least 4 carbon atoms to which are attached at least 3 hydroxyl groups, the polyether containing more than one alkenyl group per molecule. Other monoolefinic monomeric materials may be present in the monomeric mixture if desired, even in predominant proportion. Carboxyvinylpolymers are substantially insoluble in liquid, volatile organic hydrocarbons and are dimensionally stable on exposure to air.

Preferred polyhydric alcohols used to produce carboxyvinylpolymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least 2 allyl ether groups per polyol molecule. When the polyol is sucrose, it is preferred that the sucrose have at least about 5 allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing carboxyvinylpolymers used herein include monomeric, polymerizable, alpha-beta monoolefinically unsaturated lower aliphatic carboxylic acids; more preferred are monomeric monoolefinic acrylic acids of the structure:

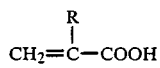

where R is a substituent selected from the group consisting of hydrogen and lower alkyl groups; most preferred is acrylic acid.

Preferred carboxyvinylpolymers used in formulations of the present invention have a molecular weight of at least about 750,000; more preferred are carboxyvinylpolymers having a molecular weight of at least about 1,250,000; most preferred are carboxyvinylpolymers having a molecular weight of from about 2,500,000 to about 4,500,000.

Various carboxyvinylpolymers are commercially available from B. F. Goodrich Company, New York, N.Y., under the tradename Carbopol. Carboxyvinylpolymers preferred for use in the sustained pharmaceutical capsules of the present invention include Carbopol 940 having a molecular weight of about 4,000,000 and Carbopol 941 having a molecular weight of about 1,250,000. Highly preferred Carbopol 934 is a very slightly cross-linked carboxyvinylpolymer having a molecular weight of about 3,000,000. It has been described as a high molecular weight polyacrylic acid cross-linked with about 1% of polyallyl sucrose having an average of about 5.8 allyl groups for each molecule of sucrose.

The primary function of the carboxyvinylpolymer in the sustained release pharmaceutical capsules of the present invention is to control the duration of the sustained release of the nitrofurantoin. As the percentage of carboxyvinylpolymer in the particulate mixture is increased, the duration of sustained release of the nitrofurantoin increases; therefore, the percentage of carboxyvinylpolymer is adjusted to achieve the desired sustained release rate of the nitrofurantoin.

The particulate mixture of the sustained release pharmaceutical capsules of the present invention comprise from about 4% to about 40% of carboxyvinylpolymer, preferably from about 5% to about 25% of carboxyvinylpolymer, more preferably from about 6% to about 15% of carboxyvinylpolymer, more preferably still from about 7% to about 10% of carboxyvinylpolymer. The particle size of the carboxyvinylpolymer in the particulate mixture preferably is such that 100 percent of particles will pass through a 60 mesh sieve (U.S. Standard Screen). (Due to adherence of carboxyvinylpolymer particles to one another, force may be required to pass the carboxyvinylpolymer particles through such sieve.)

Optional Ingredients

For the combination sustained release/rapid release pharmaceutical capsules of the present invention, necessary ingredients are the nitrofurantoin, polyvinylpyrrolidone, and carboxyvinylpolymer as described hereinabove. Other pharmaceutical carriers may be added to provide capsules having the desired characteristics or as production aids. By "pharmaceutical carrier" as used herein, is meant one or more compatible solid filler diluents or solid or liquid substances added to aid in the production of the capsules, such as lubricants to reduce friction and glidants to improve flow of the particulate mixtures. By "compatible" as used herein, is meant that the components are capable of being comingled without interacting in a manner which would substantially decrease the pharmaceutical efficacy of the capsules under ordinary use situations.

Some examples of substances which can serve as pharmaceutical carriers are sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; zinc stearate; calcium sulphate; silicon dioxide; vegetable oils, such as peanut oil, cottonseed oil, sesame oil, olive oil, corn oil and oil of theobroma; polyols, such as propylene glycol, glycerine, sorbitol, mannitol, and polyethylene glycol; agar; and alginic acid; as well as other non-toxic compatible substances used in pharmaceutical formulations. Wetting agents such as sodium laural sulphate, as well as coloring agents, lubricants, excipients, stabilizers, antioxidants, and preservatives, can also be present.

Capsule Shells

The combination sustained release/rapid release nitrofurantoin capsules of the present invention comprise particulate mixtures in a capsule shell which is soluble in a gastrointestinal juice. The preferred capsule shells used for capsules of the present invention are hard gelatin capsules. Hard gelatin capsules are soluble in gastric juice. As described hereinabove, dissolution of the capsule shell results in the layer of the second particulate mixture dispersing rapidly thus making the macrocrystalline nitrofurantoin contained therein available for rapid absorption into the systemic system. The first particulate mixture of the combined sustained release/rapid release capsules forms a cohesive mass which is eroded very little in gastric juice. Hard gelatin capsule shells thus provide the needed structure to deliver the sustained release portion of the capsules to the intestines where sustained release of the nitrofurantoin contained therein occurs.

If it were desired to prevent any release of nitrofurantoin in the stomach, a capsule shell or caoted capsule shell could be used whose solubility is pH dependent such that the capsule shell or coating does not dissolve until it reaches the intestines. The rapid release portion of the nitrofurantoin would thus be released in the intestines followed by the sustained release of nitrofurantoin from the sustained release portion of the capsules. However, for most purposes, it is preferable to have the rapid release portion of macrocrystalline nitrofurantoin dispersed in the stomach in order to achieve systemic absorption of nitrofurantoin more rapidly.

Process for Producing the Combination Sustained Release/Rapid Release Capsules

The combination sustained release/rapid release nitrofurantoin capsules are preferably produced by a process comprising the steps of: (1) preparing a first particulate mixture, said first particulate mixture being the same as for the sustained release portion of the nitrofurantoin capsules described hereinabove; (2) preparing a second particulate mixture comprising macrocrystalline nitrofurantoin; and (3) filling, into a capsule shell, a first layer of said first particulate mixture, and a second layer of said second particulate mixture. The combination sustained release/rapid release nitrofurantoin capsules of the present invention can be easily and inexpensively produced using standard pharmaceutical industry mixing and capsule-filling equipment.

Two separate particulate mixtures are produced. The first particulate mixture comprises nitrofurantoin, polyvinylpyrrolidone, and carboxyvinylpolymer raw materials which are each preferably obtained in solid, particulate form, either as granules or powders. These separate raw materials are preferably powders.

The nitrofurantoin, polyvinylpyrrolidone, carboxyvinylpolymer, and any pharmaceutical carrier powder components are preferably dry blended until the particulate mixture is substantially uniform in composition.

For a pharmaceutical carrier which is to be incorporated in the first particulate mixture as a liquid, such liquid may be incorporated by spraying or other addition means and blending the first particulate mixture until the liquid is unformly dispersed therein. Although some liquid may thus be added to the first particulate mixture, it retains its flowable, particulate form.

The second particulate mixture comprises macrocrystalline nitrofurantoin, and preferably any pharmaceutical carriers as described hereinbefore needed to provide a second particulate mixture which can be readily filled into capsules using a capsule-filling machine, and such that the second particulate mixture will rapidly disperse in the gastrointestinal juice when the capsule shell dissolves. The formulation of such second particulate mixtures is well within the purview of a person skilled in the art of formulating pharmaceutical capsule compositions.

The sustained release (first particulate) and rapid release (second particulate) mixtures are then filled into a capsule shell in separate layers, preferably using standard pharmaceutical capsule-filling machines. The order in which the sustained release and rapid release mixtures are filled into the capsule shell is not important. For the combination sustained release/rapid release nitrofurantoin capsules, it is preferred that there be a single layer of sustained release (first particulate) mixture and a single layer of rapid release (second particulate) mixture. However, more than one layer of either or both of the mixtures could be included in such capsules.

The following nonlimiting examples describe combination sustained release/rapid release nitrofurantoin capsules of the present invention and processes for producing them.

EXAMPLE 1

Combination sustained release/rapid release nitrofurantoin capsules of the present invention are made according to the following formulation:

| Ingredient | Sustained Release Mixture | | |
|---|---|---|---|
| | Weight per Batch (g) | Weight Per Capsule (mg) | Weight Percent |
| Nitrofurantoin monohydrate | 15.00 | 150.0 | 49.3 |
| Carbopol 934P | 1.77 | 17.7 | 5.8 |
| PVP C-15 | 13.10 | 131.0 | 43.1 |
| Talc | 0.35 | 3.5 | 1.2 |
| Zinc Stearate | 0.18 | 1.8 | 0.6 |
| Total | 30.40 | 304.0 | 100.0 |

The Carbopol 934P (pharmaceutical grade of Carbopol 934, B. F. Goodrich Chemical Company, Cleveland, Ohio), PVP C-15 (mean molecular weight of about 8,000, GAF Corporation, Wayne, N.J.), talc, and zinc stearate are combined in a mortar and triturated well. The nitrofurantoin monohydrate (Norwich Eaton Pharmaceuticals, Inc., Norwich, N.Y. is added to this mixture in the mortar and triturated well until a substantially uniform first particulate mixture is achieved.

The resulting first (sustained release) particulate mixture is hand filled as a first layer into size 1 hard gelatin capsule shells. A second layer of 50 mg of macrocrystalline nitrofurantoin (rapid release particulate mixture) is hand filled into each such capsule on top of the first layer. The resulting capsules provide a combined rapid release/sustained release dosage unit form of nitrofurantoin.

EXAMPLE 2

Combination sustained release/rapid release nitrofurantoin capsules of the present invention are made according to the following formulation:

| Ingredient | Sustained Release Mixture | | |
|---|---|---|---|
| | Weight per Batch (g) | Weight Per Capsule (mg) | Weight Percent |
| Nitrofurantoin anhydrous acid | 15.00 | 150.0 | 59.0 |
| Carbopol 934P | 2.66 | 26.6 | 10.5 |
| PVP K-90 | 7.21 | 72.1 | 28.4 |
| Talc | 0.35 | 3.5 | 1.4 |
| Zinc Stearate | 0.18 | 1.8 | 0.7 |
| Total | 25.40 | 254.0 | 100.0 |

A first particulate mixture of nitrofurantoin (anhydrous acid, Norwich Eaton Pharmaceuticals, Inc., Norwich, N.Y.) PVP K-90 (mean molecular weight of about 630,000, GAF Corporation, Wayne, N.J.) and the other ingredients above is prepared according to the method described in Example 1. Macrocrystalline nitrofurantoin (100 mg per capsule) is used as the rapid release particulate mixture and capsules are prepared according to the method described in Example 1. The resulting capsules provide a combined rapid release/sustained release dosage unit form of nitrofurantoin.

EXAMPLE 3

Combination sustained release/rapid release nitrofurantoin capsules of the present invention are made according to the following formulation:

| Ingredient | Sustained Release Mixture | | |
|---|---|---|---|
| | Weight per Batch (g) | Weight Per Capsule (mg) | Weight Percent |
| Nitrofurantoin monohydrate | 15.00 | 150.0 | 49.3 |
| Carbopol 941 | 5.31 | 53.1 | 17.5 |
| PVP C-15 | 9.56 | 95.6 | 31.4 |
| Talc | 0.35 | 3.5 | 1.2 |
| Zinc Stearate | 0.18 | 1.8 | 0.6 |
| Total | 30.40 | 304.0 | 100.0 |

A first particulate mixture of sodium nitrofurantoin (Norwich Eaton Pharmaceuticals, Inc., Norwich, N.Y.), Carbopol 941 (B. F. Goodrich Co.) and the other ingredients above is prepared according to the method described in Example 1. Macrocrystalline nitrofurantoin (50 mg per capsule) is used as the rapid release particulate mixture and capsules are prepared according to the method described in Example 1. The resulting capsules provide a combined rapid release/sustained release dosage unit form of nitrofurantoin.

EXAMPLE 4

Combination sustained release/rapid release nitrofurantoin capsules of the present invention are made according to the following formulation:

| Ingredient | Sustained Release Mixture | | |
|---|---|---|---|
| | Weight per Batch (g) | Weight Per Capsule (mg) | Weight Percent |
| Nitrofurantoin monohydrate | 15.00 | 150.0 | 45.6 |
| Carbopol 934P | 8.85 | 88.5 | 26.9 |
| PVP C-15 | 8.52 | 85.2 | 25.9 |
| Talc | 0.35 | 3.5 | 1.1 |
| Zinc Stearate | 0.18 | 1.8 | 0.5 |
| Total | 32.90 | 329.0 | 100.0 |

A first particulate mixture of the above ingredients is prepared according to the methods described in Example 1. Macrocrystalline nitrofurantoin (25 mg per capsule) is used as the rapid release particulate mixture and capsules are prepared according to the method described in Example 1. The resulting capsules provide a combined rapid release/sustained release dosage unit form of nitrofurantoin.

EXAMPLE 5

Combination sustained release/rapid release nitrofurantoin capsules of the present invention are made according to the following formulation:

| Ingredient | Sustained Release Mixture | | |
|---|---|---|---|
| | Weight per Batch (g) | Weight Per Capsule (mg) | Weight Percent |
| Nitrofurantoin monohydrate | 1614 | 161.4 | 45.6 |
| Carbopol 934P | 283.2 | 28.32 | 8.0 |
| PVP K-29/32 | 881.7 | 88.17 | 24.9 |
| Talc | 35.4 | 3.54 | 1.0 |
| Cabosil | 35.4 | 3.54 | 1.0 |
| Dipac | 619.5 | 61.95 | 17.5 |
| Magnesium Stearate | 70.8 | 7.08 | 2.0 |
| Total | 3540 | 354.0 | 100.0 |

The nitrofurantoin monohydrate, Carbopol 934P (B. F. Goodrich Chemical Co., Cleveland, Ohio). PVP K-29/32 (mean molecular weight of about 40,000, GAF Corporation, Wayne, N.J.) Cabosil (colloidal silicon dioxide, Commercial Chemicals. Inc., Buffalo, N.Y.), and talc are blended in a V-blender (Patterson-Kelly Co., East Stroudsburg, Pa.) for 10 minutes. The mixture is then sifted through a 60 mesh sieve (U.S. Standard Screen) using a Stokes Oscillating Granulator (Model 900-43-G, Sharples-Stokes Division, Pennwait Corp., Warminster, Pa.) in order to eliminate any agglomerates or lumps of material; lumps are broken up and all material is forced through the screen. The mixture is further blended in the V-blender with sequential addition of the Dipac (compressible sugar, Amstar Corp., Brooklyn, N.Y.) and magnesium stearate until a substantially uniform first particulate mixture is obtained.

| Ingredient | Rapid Release Mixture | | |
|---|---|---|---|
| | Weight Per Batch (g) | Weight Per Capsule (mg) | Weight Percent |
| Macrodantin ® | 500 | 50.0 | 15.4 |
| Talc | 230 | 23.0 | 7.1 |
| Starch | 380 | 38.0 | 11.7 |
| Lactose, hydrous | 2140 | 214.0 | 65.8 |
| Total | 3250 | 325.0 | 100.0 |

The rapid release particulate mixture is prepared by adding the Macrodantin ® (Norwich Eaton Pharmaceuticals, Inc., Norwich, N.Y.) and the other above ingredients to a V-blender and mixing for 10 minutes.

Capsules are prepared by first filling 325 mg of the rapid release particulate mixture as a first layer into size 0 hard gelatin capsule shells using a commercial capsule filling machine (Harro Hofliger Model KFM/3, M.O. Industries, East Hanover, N.J.). After such first layer is filled into the capsule shells, the resulting partially filled capsules are again fed into the capsule filling machine and 354 mg of the sustained release particulate mixture is filled into each capsule shell as a second layer on top of the rapid release particulate mixture.

Samples of the capsules are subjected to dissolution testing using USP Apparatus 2 (U.S. Pharmacopeia XXI, 1985, pp. 1243–1244), paddle speed 100 rpm, temperature 37° C., in simulated gastric fluid (SGF), pH 1.2 (U.S. Pharmacopeia XXI, 1985, p. 1424), as dissolution medium for the first hour, and then in simulated intestinal fluid (SIF), pH 7.5 (U.S. Pharmaceoeia XXI, 1985, p. 1424), as dissolution medium for the remainder of the test. Samples are taken from the dissolution medium at time 0 and at each ½ hour interval and are assayed for nitrofurantoin until 90% of the total capsule dose is found to be in solution. The SGF and SIF are the same as provided for in the USP except that they do not contain the enzymes. Capsules are weighted down in the dissolution flask by coiling a wire around them.

The nitrofurantoin is assayed in the dissolution media by monitoring samples of the medium spectrophotometrically, at 367 nm for SGF and at 383 nm for SIF and comparing with calibrated solutions of known nitrofurantoin content.

The rapid release performance of the capsules of this example is demonstrated in this test by the presence of 15% of the total capsule nitrofurantoin dose being in solution after one hour; the sustained release performance is demonstrated by the 6 hours required to achieve 90% of the total capsule nitrofurantoin dose in solution.

While particular embodiments of the present invention have been described, it will be obvious to those skilled in the art that various changes and modifications of the nitrofurantoin capsules of the present invention and the processes for producing them can be made without departing from the spirit and scope of the invention. It is intended to cover, in the appended claims, all such modifications that are within the scope of this invention.

What is claimed is:

1. A controlled release pharmaceutical composition for oral administration of nitrofurantoin to a human subject, comprising:
   (1) a first layer of a first flowable, particulate mixture consisting essentially of
   (a) from about 10% to about 90% of nitrofurantoin
   (b) from about 5% to about 86% of polyvinylpyrrolidone; and
   (c) from about 4% to about 40% of carboxyvinylpolymer; wherein said polyvinylpyrrolidone and said carboxyvinylpolymer occur substantially entirely in separate particles of said first particulate mixture; and
   (2) a second layer of a second flowable, particulate mixture comprising macrocrystalline nitrofurantoin;

in a capsule shell which is soluble in gastrointestinal juice, wherein said composition, when administered to said subject, provides rapid release and sustained release of nitrofurantoin with low incidence of nausea and emesis.

2. The capsule of claim 1 wherein said first particulate mixture comprises from about 10% to about 70% of polyvinylpyrrolidone, and said capsule shell is soluble in gastric juice.

3. The capsule of claim 1 wherein said first particulate mixture comprises from about 15% to about 60% of polyvinylpyrrolidone, and said capsule shell is a hard gelatin capsule shell which is soluble in gastric juice.

4. The capsule of claim 2 wherein said first particulate mixture comprises from about 5% to about 25% of carboxyvinylpolymer.

5. The capsule of claim 3 wherein said first particulate mixture comprises from about 20% to about 70% of nitrofurantoin acid, or a hydrate thereof, and from about 5% to about 15% of carboxyvinylpolymer.

6. The capsule of claim 2 wherein said first particulate mixture comprises from about 30% to about 70% of nitrofurantoin acid, or a hydrate thereof, and from about 7% to about 10% of carboxyvinylpolymer.

7. The capsule of claim 4 wherein said carboxyvinylpolymer has a molecular weight of at least about 1,250,000, and said capsule shell is a hard gelatin capsule shell.

8. The capsule of claim 5 wherein said carboxyvinylpolymer has a molecular weight of about 3,000,000 and is a polyacrylic acid cross-linked with about 1% of polyallyl sucrose having an average of about 5.8 allyl groups for each molecule of sucrose.

9. The capsule of claim 6 wherein said carboxyvinylpolymer has a molecular weight of about 3,000,000 and is a polyacryllic acid cross-linked with about 1% of polyallyl sucrose having an average of about 5.8 allyl groups for each molecule of sucrose.

10. The capsule of claim 8 where said polyvinylpyrrolidone has a molecular weight of from about 7,000 to about 700,000.

* * * * *